(12) United States Patent
Lloyd et al.

(10) Patent No.: US 7,005,261 B1
(45) Date of Patent: Feb. 28, 2006

(54) METHOD FOR DETECTING NUCLEIC ACID TARGET SEQUENCES INVOLVING IN VITRO TRANSCRIPTION FROM AN RNA POLYMERASE PROMOTER

(75) Inventors: John Scott Lloyd, King Sutton (GB); Anthony Weston, Northolt (GB); Donald Leonard Nicholas Cardy, Aston-le-Walls (GB)

(73) Assignee: British Biocell International Limited, Cardiff (GB)

( * ) Notice: Subject to any disclaimer, the term of this patent is extended or adjusted under 35 U.S.C. 154(b) by 630 days.

(21) Appl. No.: 10/048,225

(22) PCT Filed: Jul. 31, 2000

(86) PCT No.: PCT/GB00/02962

§ 371 (c)(1),
(2), (4) Date: Jul. 31, 2002

(87) PCT Pub. No.: WO01/09377

PCT Pub. Date: Feb. 8, 2001

Related U.S. Application Data

(60) Provisional application No. 60/149,176, filed on Jul. 31, 1999.

(30) Foreign Application Priority Data

Jul. 29, 1999 (GB) .................................. 9917813

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6, 435/91.2; 536/23.1, 24.3
See application file for complete search history.

(56) References Cited

FOREIGN PATENT DOCUMENTS

| EP | 0 552 931 A1 | 7/1993 |
|---|---|---|
| EP | 0 851 033 A1 | 7/1998 |
| WO | WO 93/06240 | 4/1993 |
| WO | WO 99/37805 | 7/1999 |
| WO | WO 99/37806 | 7/1999 |

*Primary Examiner*—Ethan Whisenant
(74) *Attorney, Agent, or Firm*—Morgan, Lewis & Bockius, LLP

(57) ABSTRACT

Disclosed is a complex formed by a hybridization reaction comprising four nucleic acid molecules; the complex comprising a target nucleic acid molecule and first, second and third nucleic acid probe molecules; wherein the first probe comprises a foot region which is complementary to a first portion of the target and is hybridized thereto, and an arm region which is substantially non-complementary to the target; the second probe comprises a foot region which is complementary to a second portion of the target, such that the foot region of the second probe is hybridized to the target adjacent or substantially adjacent to the foot region of the first probe, the second probe also comprising an arm region which is substantially non-complementary to the target but which is complementary and hybridized to the arm region of the first probe; the third probe being complementary, at least in part, to a portion of the arm region of the first probe, such that third probe is hybridized to the arm region of the first probe adjacent or substantially adjacent to the second probe; and wherein formation of the complex creates a functional double-stranded RNA polymerase promoter, one strand of the promoter being provided by the first probe, and the other strand being provided jointly by the second probe and by the third probe; and a method of detecting a target nucleic acid sequence of interest which method involves the formation of the complex.

18 Claims, 10 Drawing Sheets

METHOD FOR DETECTING NUCLEIC ACID TARGET SEQUENCES INVOLVING IN VITRO TRANSCRIPTION FROM AN RNA POLYMERASE PROMOTER

This application claims benefit of Provisional Application No. 60/149,176, filed Jul. 31, 1999.

FIELD OF THE INVENTION

This invention relates to nucleic acid complexes comprising a functional RNA polymerase promoter, and to a method of detecting a target nucleic acid sequence of interest.

BACKGROUND OF THE INVENTION

RNA polymerases are enzyme molecules well-known to those skilled in the fields of molecular biology and molecular diagnostic kits. RNA polymerases synthesise RNA molecules from a DNA template strand.

Much research has been carried out on RNA polymerases, especially bacteriophage RNA polymerases.

Specifically, the RNA polymerase from the bacteriophage T7 has been shown to be very selective for specific promoters that are rarely encountered in DNA unrelated to T7 DNA (Chamberlin et al, 1970 Nature 228, 227; Dunn & Studier 1983 J. Mol. Biol. 166, 477). T7 RNA polymerase is able to make complete transcripts of almost any DNA that is placed under control of a T7 promoter. T7 RNA polymerase is a highly active enzyme that transcribes about five times faster than does *Escherichia coli* RNA polymerase (Studier et al, 1990 Methods Enzymol. 185, 60). The synthesis of small RNAs using T7 RNA polymerase has been described whereby sequences around the RNA polymerase promoter sequence are shown to be important in the reproducible improvement of yield of RNA produced (Milligan & Uhlenbeck, 1989 Methods Enzymol. 180, 51 and Milligan et al, 1987 Nucl. Acids Res. 15, 8783–8798). Other RNA polymerases that have similar properties to T7 include those from bacteriophage T3 and SP6, the genes for which have all been cloned and the corresponding enzymes are commercially available. The optimum promoter sequences for T7, T3 and SP6 polymerases are known, and are essentially 17 nucleotides long.

A number of methods have been disclosed, which utilise RNA polymerases to synthesise RNA directly or indirectly as the result of the presence of a particular nucleic acid sequence of interest ("target"). The presence of RNA (detected directly or indirectly) thus serves to signal the presence of the sequence of interest and can be used as the basis of assay methods and/or diagnostic methods or kits. Examples include the disclosures of WO 93/06240, WO 94/29481, EP 0851033, and EP 0552931.

In particular WO 93/06240 discloses the use of two probes, which hybridise together only in the presence of a target nucleic acid sequence of interest, such that hybridisation of the probes to each other is indicative of the presence of the sequence of interest.

All publications mentioned in this specification are incorporated herein by reference.

SUMMARY OF THE INVENTION

In a first aspect the invention provides a complex formed by a hybridisation reaction comprising four nucleic acid molecules; the complex comprising a target nucleic acid molecule and first, second and third nucleic acid probe molecules; wherein the first probe comprises a foot region which is complementary to a first portion of the target and is hybridised thereto, and an arm region which is substantially non-complementary to the target; the second probe comprises a foot region which is complementary to a second portion of the target, such that the foot region of the second probe is hybridised to the target adjacent or substantially adjacent to the foot region of the first probe, the second probe also comprising an arm region which is substantially non-complementary to the target but which is complementary and hybridised to the arm region of the first probe; the third probe being complementary, at least in part, to a portion of the arm region of the first probe, such that the third probe is hybridised to the arm region of the first probe adjacent or substantially adjacent to the second probe; and wherein formation of the complex creates a functional double-stranded RNA polymerase promoter, one strand of the promoter being provided by the first probe, and the other strand being provided jointly by the second probe and by the third probe.

Preferably the sequence of the probes and the hybridisation reaction conditions are selected such that the first and second probes cannot become hybridised in the absence of the target, such that formation of the RNA polymerase promoter occurs in a target-dependent manner.

In a second aspect, the invention provides a method of detecting the presence of a target nucleic acid molecule in a sample, the method comprising the steps of contacting the sample comprising the target with first and second nucleic acid probes, each probe comprising a foot region complementary to respective first and second portions of the target, which portions are adjacent or substantially so; wherein the first and second probes each further comprise an arm region substantially non-complementary to the target, at least part of the arm region of the first probe being complementary to at least part of the arm region of the second probe, such that respective foot regions of the first and second probes hybridise to the target, allowing hybridisation of the complementary parts of the arm regions of the first and second probes; and causing to be present a third nucleic acid probe molecule which is complementary to a portion of the arm region of the first probe, such that the third probe hybridises to the first probe adjacent or substantially adjacent to the arm region of the second probe, thereby creating a functional double-stranded RNA polymerase promoter, one strand of the promoter being provided by the first probe, the other strand being provided jointly by the second and third probes; causing RNA synthesis from the RNA promoter; and detecting, directly or indirectly, the RNA so synthesised.

The method of the second aspect of the invention thus results in formation of the complex of the first aspect.

It is an essential feature of the invention that the first and second probes, when hybridised to the target sequence, are adjacent or substantially adjacent to each other. Use of the term "adjacent" is herein intended to mean that there are no nucleotides of the target sequence left without base-pairing between those portions of the target sequence which are base-paired to the complementary sequence of the probes. This proximity between the probes enables the complementary arm portions of the probes to anneal. As will readily be apparent to those skilled in the art, by designing the probes so as to allow for annealing to each other at greater separations from the target sequence, gaps may be introduced between the loci in the target nucleotide sequence to which the probes hybridise. In this situation the probes are said to be "substantially adjacent", because there may be some nucleotides of the target sequence left without base-pairing between those portions of the target sequence which are base-paired to the probes. Clearly, the number of intervening un-paired nucleotides of the target sequence can vary according to the design of the probes. Thus whilst it is preferred that the first and second probes hybridise so as to be adjacent, the probes may be separated by up to 5 nucleotides of target sequence, and the term "substantially adjacent" is intended to refer to such situations.

It will also be appreciated from the foregoing that the second and third probes must hybridise to the arm region of the first probe such that the second and third probes are "adjacent", or substantially so, which terms are intended to have the same meanings as defined above. However, as the second and third probes together constitute one strand of the promoter, it is very much to be desired that they hybridise in an adjacent manner so as to provide optimum promoter activity: the inventors have found that the amount of promoter activity is greatly reduced even if a single nucleotide gap occurs between the second and third probes.

It will be apparent to those skilled in the art that the order of addition of probes in the formation of the nucleic acid complex is not critical: the third probe may, for example, be hybridised to the first probe before the second probe and sample are added. Alternatively, for example, all three probes may be simultaneously mixed with the sample containing the target molecule.

It will be further apparent to those skilled in the art that the second and third probes, which jointly provide one of the strands of the RNA polymerase promoter, are not covalently joined and the promoter sequence thus contains a "nick" in the phosphodiester backbone of one of the strands. For the sake of clarity, it is mentioned that the aforementioned first, second and third probes are elsewhere described and referred to in this specification as "template", "complement" and "split complement" respectively.

Preferred promoters for use in the invention are those recognised by bacteriophage polymerases, especially those promoters recognised by one of T3, T7 or SP6 polymerase. These will generally comprise a minimum of 17 or 18 bases, essentially double-stranded. The sequence of the double-stranded T3 RNA polymerase promoter (described in the prior art) is:

```
i)  5' AATTAACCCTCACTAAA 3'
    3' TTAATTGGGAGTGATTT 5'
or
ii) 5' TTA TTA ACC CTC ACT AAA 3'
    3' AAT AAT TGG GAG TGA TTT 5'
i)   = Seq ID No. 1
ii)  = Seq ID No. 2
```

(A number of variant T3 promoter sequences are also known, especially those in which the first three bases of the non-template strand [the upper strand shown above] are 5' TTA 3', rather than AAT.)

The sequence of the T7 RNA polymerase promoter (described in the prior art) is:

```
5' TAATACGACTCACTATA 3'     (Seq ID No. 3)
3' ATTATGCTGAGTGATAT 5'
```

The sequence of the SP6 RNA polymerase promoter (described in the prior art) is:

```
5' ATTTAGGTGACACTATA 3'     (Seq ID No. 4)
3' TAAATCCACTGTGATAT 5'
```

One of the strands of the promoter is provided by the first probe. Typically this will be the "sense" (+) strand, which is transcribed by the polymerase. Accordingly the first probe will generally comprise a stretch of "template" nucleic acid to be transcribed. The template will desirably comprise sequences which facilitate capture (e.g. hybridisation) of the resulting RNA transcript and/or detection. In addition, the first probe may desirably contain sequences (e.g. a "+12 sequence") adjacent to the promoter sequence, which serve to increase the activity of the promoter. Specific instances of such sequences are disclosed in the examples below. A "+12 sequence" is so-termed because it consists of 12 bases immediately downstream (i.e. at positions +1 to +12) of the promoter, and causes enhanced transcription levels.

The inventors have elucidated the optimum sequence of +12 regions for the T7 polymerase (discussed in greater detail below)—it is not known at present if these are also optimum for, say, T3 and SP6 polymerases. If, as is possible, SP6 and T3 polymerases have different optimum +12 regions, it would be a simple matter for the person skilled in the art to identify the relevant sequence by trial-and-error, with the benefit of the present disclosure.

The sequences of preferred +12 regions, for inclusion in the template portion of the first probe, (in respect of T7 polymerase) are shown below in Table 1. The most active +12 region (giving greatest transcription) is at the top, with the other sequences shown in decreasing order of preference.

Table 1 Alternative template +1 to +12 sequences for T7 polymerase, in descending order of transcription efficiency (Seq ID Nos. 5–14).

```
5' ATCGTCAGTCCC 3'

5' GCTCTCTCTCCC 3'

5' ATCCTCTCTCCC 3'

5' GTTCTCTCTCCC 3'

5' GATGTGTCTCCC 3'

5' GTTGTGTCTCCC 3'

5' ATCCTCGTGCCC 3'

5' GCTCTCGTGCCC 3'

5' GTTCTCGTGCCC 3'

5' GTTGTGGTGCCC 3'
```

(The 5 base is numbered as +1, being the first base downstream from the end of the promoter sequence, the 3 base as +12).

In a further embodiment, the template portion of the complex (generally on the first probe) could contain sequences that can be used to isolate, identify, detect, quantify or amplify the de novo synthesised RNA transcripts (see, for example, WO 93/06240, U.S. Pat. No. 5,554,516, or, for example, using molecular beacon sequences such as those disclosed by Tyagi & Kramer 1996 Nature Biotech 14, 303–308). These sequences are conveniently placed adjacent to, and downstream of, a +12 region (as described above) and may comprise, but are not limited to, one or more of the following: unique "molecular beacon" sequences; capture sequences; and detection probe complementary sequences.

In principle, the seventeen bases of the promoter sequence may be partitioned between the second and third probes in any manner, provided that, in combination, the second and third probes provide one strand of the full promoter sequence. In practice, the inventors have found that optimum results are generally obtained when the second probe provides 2 to 4 (preferably 3) bases at the 5' end of the promoter sequence, with the rest of the promoter (15 to 13 bases) being contributed by the third probe. In addition, the inventors have found that promoter activity may be enhanced by including some additional bases (typically 1–3 bases or more) at the 3' end of the third probe (e.g. by providing at least some bases complementary to the +12 sequence on the template strand, so that the +12 sequence becomes at least partially double stranded).

Any of the first, second or third probes may comprise DNA, peptide nucleic acid (PNA), locked nucleic acid (LNA), (less preferably RNA) or any combination thereof. It will, however, generally be desirable that those portions of the probes which constitute the promoter comprise conventional DNA, so as to ensure recognition by the relevant polymerase. The terms "nucleic acid complex", "nucleic acid molecule" and "nucleic acid probe" should accordingly not be construed as being limited to complexes, molecules or probes (respectively) which consist solely of conventional nucleic acid, but also encompass complexes, molecules or probes which comprise non-conventional nucleic acid (such as PNA or LNA) or non-nucleic acid portions.

PNA is a synthetic nucleic acid analogue in which the sugar/phosphate backbone is replaced by a peptide-linked chain (typically of repeated N-(2-aminoethyl)-glycine units), to which the bases are joined by methylene carbonyl linkages. PNA/DNA hybrids have high Tm values compared to double stranded DNA molecules, since in DNA the highly negatively-charged phosphate backbone causes electrostatic repulsion between the respective strands, whilst the backbone of PNA is uncharged. Another characteristic of PNA is that a single base mis-match is, relatively speaking, more destabilizing than a single base mis-match in heteroduplex DNA. Accordingly, PNA is useful to include in probes for use in the present invention, as the resulting probes have greater specificity than probes consisting entirely of DNA. Synthesis and uses of PNA have been disclosed by, for example, Orum et al, (1993 Nucl. Acids Res. 21, 5332); Egholm et al, (1992 J. Am. Chem. Soc. 114, 1895); and Egholm et al, (1993 Nature 365, 566).

LNA is a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. However, LNA can be synthesised on conventional nucleic acid synthesising machines, whereas PNA cannot.

In addition to non-conventional nucleic acids (such as LNA, PNA or nucleic acids containing base analogues), any one or more of the probes of use in the invention may comprise one or more destabilizing moieties.

The destabilizing moiety is a chemical entity which is generally unable to undergo base pairing and hydrogen bonding in the normal manner as usually occurs when complementary strands of nucleic acid become hybridised.

All manner of molecules may be suitable for use as a destabilizing moiety, although some compounds are specifically preferred, as described below. With the benefit of the present specification, the person skilled in the art will be able to test other compounds and readily select those which confer the appropriate degree of destabilization so as to prevent the hybridization of probes in the absence of target nucleic acid of interest. Particularly preferred, as a matter of convenience, are those compounds which are commercially available in a form (e.g. as phosphoramidites) which facilitates their incorporation into synthetic oligonucleotides using conventional automated solid phase nucleic acid synthesisers.

Destabilizing moieties which cannot base pair, but which nevertheless are capable of forming flexible folds and/or hairpin structures, are especially suitable. One such preferred destabilizing moiety comprises hexaethylene glycol (abbreviated herein as "Hex") (see FIG. 5), which may be present singly or in tandem up to n times (where n can be any number 1, but conveniently has a maximum value of 5). In a particularly preferred embodiment, the third probe comprises one Hex molecule, where the number of bases opposite the destabilising moiety in the arm region of the first probe should be three to four bases. An alternative preferred destabilizing moiety comprises a plurality of alkylene (especially methylene) repeats. Particularly preferred are penta- or hexa-methylene spacers.

Other, less preferred, destabilizing moieties may alternatively be used. These include, but are not limited to, inosine, Virazole™ (N[1]-[1-D ribofuranosyl] 3-carboxamido-1,2, 4,-triazole), Nebularin™ (N[9]-[1-D ribofuranosyl]-purine), nitropyrrole, ribose, propyl or combinations of the above eg. propyl-Hex-propyl, propyl-Hex-Hex-propyl, etc. Propyl may be replaced by, for example, ethyl, butyl, pentyl, heptyl, octyl etc. The number of bases opposite the destabilizing moiety in the arm region of the reciprocal probe should be x, where x is an integer greater than or equal to 1. The exact number of bases will of course depend on the size of the destabilizing moiety and the value of n.

The following may be used as a guide: for each Hex molecule in the destabilizing moiety, the opposite probe should preferably comprise 3–4 bases (preferably 3) (i.e. X is between 3n and 4n); for each other molecule or radical mentioned above present in the destabilizing moiety, the opposite probe should preferably comprise a single base, with the exception of the following: butyl—two bases, pentyl—two bases, heptyl—three bases, and octyl—four bases.

The chemicals described above and used as destabilizing moieties are all commercially available (e.g. from Glen Research, USA).

The person skilled in the art will appreciate how to select appropriate conditions, materials and sequences for the probes, in order to ensure that the complex of the first, second and third probes (and hence formation of the functional RNA promoter) occurs in a target dependent manner. In essence, the degree of complementarity between the arm regions of the first and second probes must be such that, in the conditions employed, they will not hybridise unless stabilised by hybridisation of the respective foot regions of the first and second probes to the target.

Generally therefore, the foot regions of the first and second probes will comprise at least 10 bases, preferably at least 20 bases, and more preferably at least 25 bases. There is no upper limit on the size of the foot regions (which may, for example, comprise several kilobases). However, in practice, the probes will normally be in vitro synthesised oligonucleotides and so it will be preferred for the foot regions to comprise no more than about 75 bases.

In contrast, the number of complementary bases between the arm regions of the first and second probes will normally be no more than 25, typically less than 15, and optimally between 5 and 13 bases, such that the arm regions will not (under the assay conditions employed) become hybridised to each other in the absence of target.

In preferred embodiments, the invention provides a method of generating a signal in a target-dependent manner (i.e. creation of the complex and hence formation of the functional promoter) and causing amplification of this signal (generation of multiple RNA transcripts under the control of the promoter) in a system which may require the use of a single enzyme type (RNA polymerase), without the need for additional enzymes (e.g. DNA polymerases) to bring about the amplification. This is significant as the reaction conditions for optimum activity of RNA and DNA polymerases are generally mutually exclusive.

Detection Methods

RNA produced in accordance with the invention could be detected in a number of ways, optionally following amplification (most preferably by means of an isothermal amplification step e.g. as disclosed in U.S. Pat. No. 5,399,491 and U.S. Pat. No. 5,480,784). For example, newly-synthesised RNA could be detected in a conventional manner (e.g. by gel electrophoresis), with or without incorporation of labelled bases during the synthesis.

Alternatively, for example, newly-synthesised RNA could be captured at a solid surface (e.g. on a bead, or in a microtitre plate), and the captured molecule detected by hybridisation with a labelled nucleic acid probe (e.g. radiolabelled, or more preferably labelled with an enzyme, chromophore, fluorophore and the like). Preferred enzyme labels include horseradish peroxidase and alkaline phosphatase.

One preferred detection method involves the use of molecular beacons or the techniques of fluorescence resonance energy transfer ("FRET"), delayed fluorescence energy transfer ("DEFRET") or homogeneous time-resolved fluorescence ("HTRF"). Molecular beacons are molecules which a fluorescence signal may or may not be generated, depending on the conformation of the molecule. Typically, one part of the molecule will comprise a fluorophore, and another part of the molecule will comprise a "quencher" to quench fluorescence from the fluorophore. Thus, when the conformation of the molecule is such that the fluorophore and quencher are in close proximity, the molecular beacon does not fluoresce, but when the fluorophore and the quencher are relatively widely-separated, the molecule does fluoresce. The molecular beacon conveniently comprises a nucleic acid molecule labelled with an appropriate fluorophore and quencher.

One manner in which the conformation of the molecular beacon can be altered is by hybridisation to a nucleic acid, for example inducing looping out of parts of the molecular beacon. Alternatively, the molecular beacon may initially be in a hair-pin type structure (stabilised by self-complementary base-pairing), which structure is altered by hybridisation, or by cleavage by an enzyme or ribozyme.

FRET (Fluorescence Resonance Energy Transfer) occurs when a fluorescent donor molecule transfers energy via a nonradiative dipole—dipole interaction to an acceptor molecule. Upon energy transfer, which depends on the $R^{-6}$ distance between the donor and acceptor, the donor's lifetime and quantum yield are reduced and the acceptor fluorescence is increased or sensitised.

Another approach (DEFRET, Delayed Fluorescence Energy Transfer) has been to exploit the unique properties of certain metal ions (Lanthanides e.g. Europium) that can exhibit efficient long lived emission when raised to their excited states (excitation=337 nm, emission=620 nm). The advantage of such long lived emission is the ability to use time resolved (TR) techniques in which measurement of the emission is started after an initial pause, so allowing all the background fluorescence and light scattering to dissipate. Cy5 (Amersham Pharmacia) (excitation=620 nm, emission=665 nm) can be used as the DEFRET partner.

HTRF (see WO92/01224; U.S. Pat. No. 5,534,622) occurs where a donor (e.g. Europium) is encapsulated in a protective cage (cryptate) and attached to the 5' end of an oligomer. The acceptor molecule that has been developed for this system is a protein fluorophore, called XL665. This molecule is linked to the 3' end of a second probe. This system has been developed by Packard.

Amplification and detection of RNA or other nucleic acid molecules are further described in our prior patent applications WO 99/37805 and WO 99/37806.

In another embodiment, the newly-synthesised RNA, before or after amplification, results in formation of a ribozyme, which can be detected by cleavage of a particular nucleic acid substrate sequence (e.g. cleavage of a fluorophore/quencher dual-labelled oligonucleotide).

In a third aspect the invention provides a complex comprising three nucleic acid molecules: a target nucleic acid sequence; a first probe; and a second probe; wherein the first probe comprises, in the 5' to 3' direction, a template portion transcribable by an RNA polymerase, a template strand of an RNA polymerase promoter, and a target complementary portion which is hybridised to at least a 3' end region of the target sequence; and wherein the second probe is hybridised to the first probe adjacent or substantially adjacent to the 3' end of the target sequence, the second probe comprising part of the non-template strand complementary to the template strand of the promoter present in the first probe, the remaining part of the non-template strand of the promoter sequence being present at the 3' end of the target sequence; the arrangement being such that formation of the complex creates a functional double stranded RNA polymerase promoter with a discontinuity in the non-template strand, between the second probe and the target sequence.

Those skilled in the art will appreciate that both the second probe and the target sequence are required to hybridise to the first probe, in order to form the double stranded functional promoter. Accordingly, RNA transcripts of the template portion of the first probe are indicative of the presence in a sample of the target sequence. Thus the complex of the third aspect of the invention provides the basis for an assay for detecting the presence in a sample of a nucleic acid sequence of interest.

In a fourth aspect therefore, the invention provides a method of detecting in a sample the presence of a nucleic acid sequence of interest; the method comprising the steps of: contacting a first and second probe as defined above, with the sample, so as to form the complex of the third aspect of the invention wherein the target sequence is the sequence of interest or is formed as a result of the presence in the sample of the sequence of interest; and detecting directly or indirectly RNA transcripts of the template portion of the first probe.

The target sequence may be RNA or DNA, and may be a sequence of interest, or may be formed as a result of the presence in the sample of the sequence of interest (e.g. by PCR, or by one of the processes disclosed in one of WO 93/06240, WO 94/29481, EP 0851033 or EP 0552931). The RNA transcript is conveniently amplified and detected by means of the methods described elsewhere in this specification.

In the complex of the third aspect of the invention, and the method of the fourth aspect of the invention, the discontinuity in the non-template strand of the promoter may, in principle, occur at any position (i.e. the 3' end of the target sequence may contribute any number of bases to the promoter sequence). In practice, it is preferred that the target sequence contributes between 1 and 5 bases, more preferably 3 bases, to the promoter sequence, such that the resulting promoter has optimal activity. It is also highly preferred that the second probe hybridises to the first probe immediately adjacent to the target sequence, so that the discontinuity in the non-template strand of the promoter is as small as possible. Again, this optimises promoter activity when the complex is formed.

The invention will now be further described by way of illustrative example and with reference to the accompanying drawings, wherein.

EXAMPLE 1

This example demonstrated that T7 RNA polymerase and three oligonucleotide probes could be used to detect a specific target sequence. Probe 1 ("template") contained, sequentially, a 34 base foot region complementary to the target sequence; an 8 base overlap sequence; the 17 base template strand of the T7 promoter; a +12 sequence and a capture and probe sequence for detection. Probe 2 ("complement") comprised a 31 base foot region complementary to the target sequence; an 8 base overlap sequence and the first three bases of the complementary (or non-template) strand of the T7 promoter. Probe 3 ("split complement") contained the remaining 14 bases of the complementary (or non-template) strand of the 17 base T7 promoter sequence. The example is illustrated schematically in FIG. 1.

Figure 1:
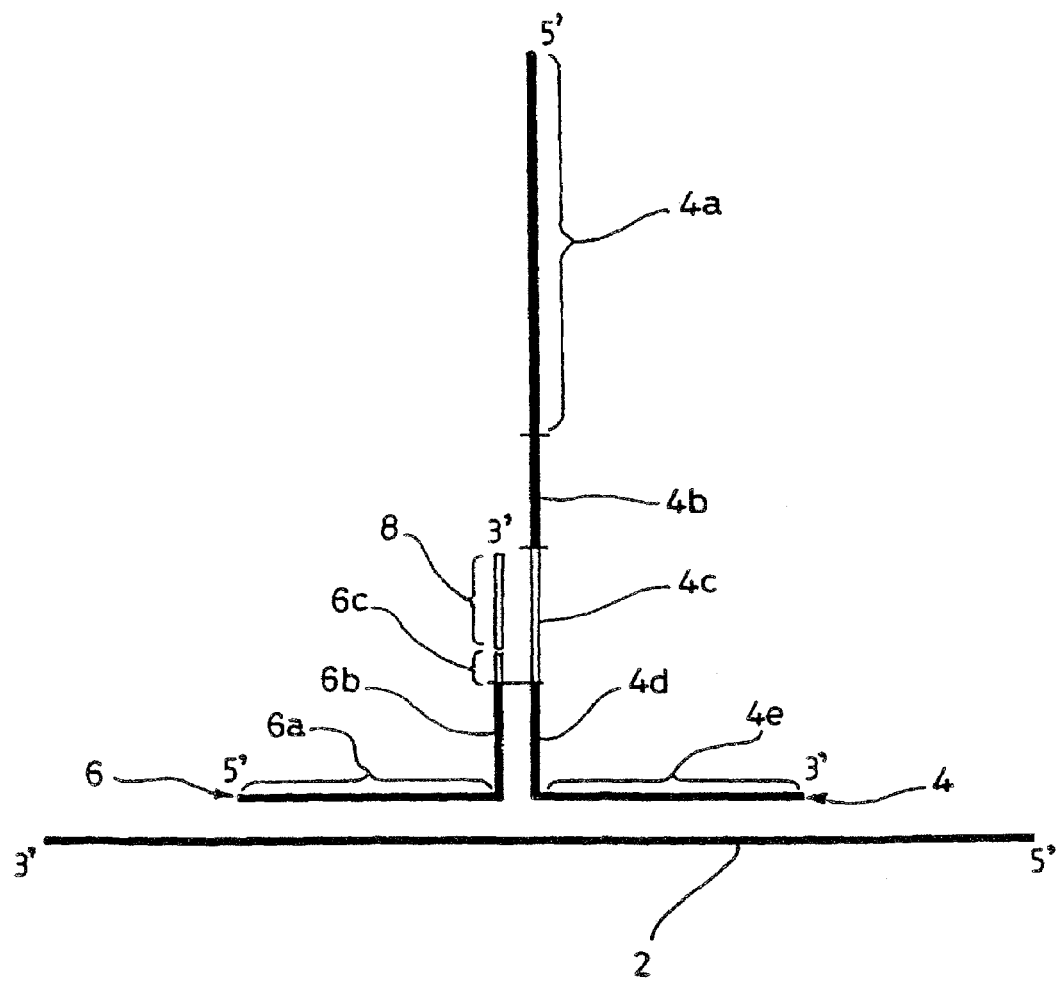
FIGS. 1 and 3 are schematic representations of a nucleic acid complex in accordance with the first aspect of the invention.

Referring to FIG. 1, a complex formed by a hybridisation reaction comprises four nucleic acid molecules: a 120 base target sequence 2, a first probe 4 ("template"), a second probe ("complement") 6, and a third probe ("split complement") 8. The orientation (5' to 3') of the four molecules 2, 4, 6 and 8 is indicated.

The first probe/template 4 comprises, in the 5' to 3' direction: a template portion 4a which facilitates isolation and detection of RNA transcripts; a +12 sequence 4b to enhance promoter activity; a promoter sequence 4c which consists of 17 bases of the T7 promoter; an overlap region 4d to hybridise to a complementary portion 6b of the second probe/complement 6; and a foot region 4e comprising 34 bases to hybridise to a complementary portion of the target 2.

The second probe/complement 6, comprises in the 5' to 3' direction: a 31 base foot region 6a to hybridise to the target; an 8 base overlap region 6b to hybridise to the complementary portion 4d of the first probe 4; and a partial promoter region 6c consisting of the first three bases (TAA) of one strand of the T7 promoter.

The third probe 8, comprises the remaining 14 bases of the T7 promoter strand.

In the presence of target 2 and probe molecules 4, 6 and 8, a complex is formed in which the foot regions of first probe 4 and second probe 6 hybridise to the target in an adjacent or substantially adjacent manner, which in turn allows the complementary overlap portions 4d and 6b to hybridise. Hybridisation of the third probe 8 to the promoter sequence 4c of the first probe thus creates a functional, double stranded T7 promoter, one of the strands of which (formed by second and third probes 6 and 8) is discontinuous.

1.1 Preparation of Oligonucleotides

All oligonucleotide probes were synthesised by phosphoramidite chemistry using an Applied Biosystems 380A synthesiser according to the manufacturer's instructions. Biotinylation of oligonucleotide probes was achieved by incorporation of a biotin phosphoratnidite. Oligonucleotides functionalised with alkaline phosphatase were prepared using the manufacturers proprietary method (Oswel). All oligonucleotides were HPLC purified using standard techniques.

1.2 Synthesis of RNA Off Hybridised Oligonucleotides

Hybridisation was achieved in an assay mixture that contained 10 fmol of probe 1, 50 fmol of probe 2, 25 fmol of probe 3 and 1 fmol of probe 4 (target for CFTR gene), together with T7 RNA polymerase buffer (Promega) (Promega; 40 mM Tris-HCl, pH 7.9, 6 mM $MgCl_2$, 2 mM spermidine, 10 mM NaCl at final concentration). The reaction volume was made up to 20 $\mu$l with RNase-free distilled water (allowing for later additions of enzymes and NTPs). Control reactions contained probes 1, 2 and 3 without target (probe 4). The mixture was heated to 90° C. for 3 minutes to denature the nucleic acids, then cooled (by ramping at 0.1° C./second) to 37° C. T7 RNA polymerase (25 units) and 2 $\mu$l rNTP mix from Amersham Pharmacia Biotech (20 mM of each r NTP: adenosine 5'-triphosphate (ATP), guanosine 5-triphosphate (GTP), cytidine 5'-triphosphate (CTP) uridine 5'-triphosphate (UTP)) were added and the mixture incubated at 37° C. for 3 hours.

1.3 Capture and Detection of Synthesised RNA

Figure 2:
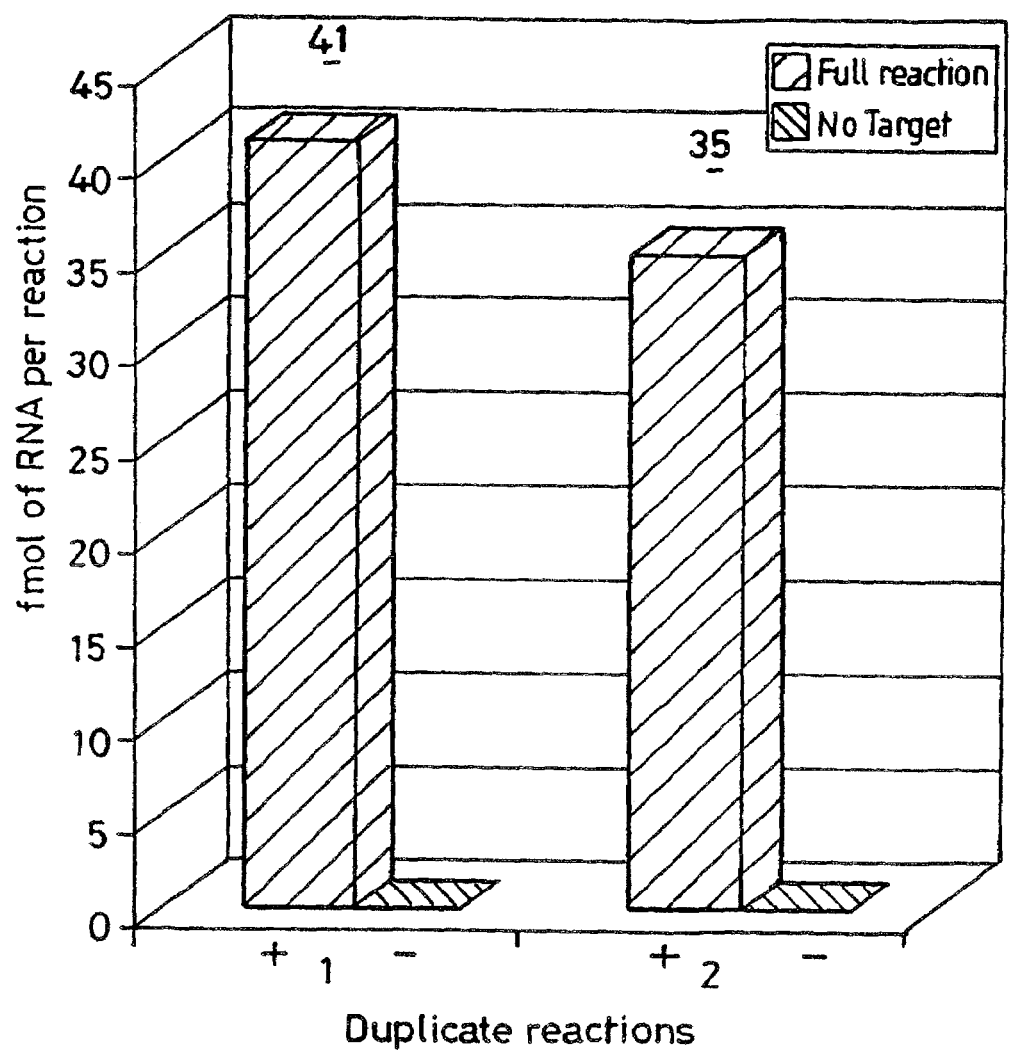
FIGS. 2, 4 and 6–9 are bar charts showing amount of RNA produced (in femtomoles) from various nucleic acid complexes.

20 $\mu$l of assay sample was added to 145 $\mu$l hybridisation buffer (50 mM Tris-HCl, pH 8.0, 1 M NaCl, 20 mM EDTA and 0.1% BSA) containing 0.9 pmol biotinylated capture oligonucleotide (specific for the RNA to be detected) and 6 pmol specific alkaline phosphatase oligonucleotide in streptavidin coated wells. Incubation (60 minutes at room temperature, shaking at 300 rpm) allowed the RNA to be immobilised on the wells via the biotinylated capture probe and annealed to the detection probe. Unbound material was removed from the wells by washing four times with TBS/ 0.1% Tween-20, then once with alkaline phosphatase substrate buffer (Boehringer Mannheim). Finally, alkaline phosphatase substrate buffer containing 4-nitrophenyl phosphate (5 mg/ml) was added to each well. The plate was incubated at 37° C. in a Labsystems EIA plate reader and readings were taken at 405 nm every 2 minutes. Results are presented in FIG. 2, which is a chart showing amount of RNA produced (in femtomoles), in the presence (+) or absence (−) of 1 fmol of target, for duplicate samples.

1.4 List of Oligonucleotides

Probe 1 (template) Seq ID No. 15

```
5'  TGCCTCCTTGTCTCCGTTCTGGATATCACCCGATGTGGCTCTCTCTCCCTA

TAGTGAGTCGTATTAATTTCGAAGGTGTTTCCTATGATGAATATAGATACAGAA

GCG 3' (phosphate blocked)
```

Probe 2 (complement) Seq ID No. 16

```
5'  GCCTGGCACCATTAAAGAAAATATCATCTTTTTCGAAATTAA 3'
```

Probe 3 (split complement) Seq ID No. 17

```
5' TACGACTCACTATA 3'
```

Probe 4 (target) Seq ID No. 18

```
5'GTTGGCATGCTTTGATGACGCTTCTGTATCTATATTCATCATAGGAAACAC

CAAAGATGATATTTTCTTTAATGGTGCCAGGCATAATCCAGGAAAACTGAGAAC

AGAATGAAATTCTTC 3'
```

Sequence of transcribed RNA Seq ID No. 19

```
5'  GGGAGAGAGAGCCACAUCGGGUGAUAUCCAGAACGGAGACAAGGAG

GCA 3'
```

Capture Probe Seq ID No. 20

```
5' TCTGCTGCCTGCTTGTCTGCGTTCT 3'
```

Detection probe Seq ID No. 21

```
5' GGATATCACCCG 3'
```

(3' alkaline phosphatase labelled)

EXAMPLE 2

Figure 3:
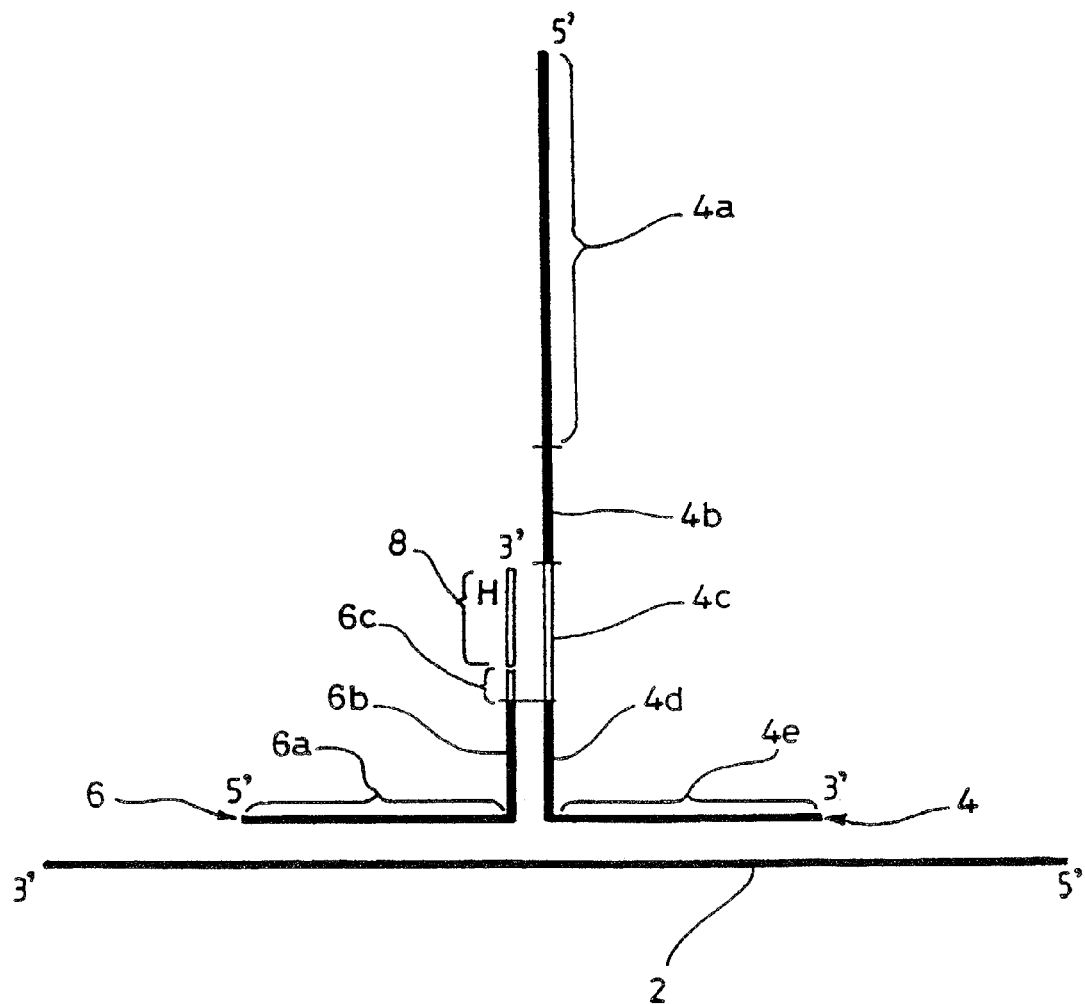

This example demonstrated that a Hexaethylene glycol linker (Hex) positioned 3 bases from the 3' end of Probe 3 (i.e. the split complement probe) increased the amount of signal obtained. The example is illustrated schematically in FIG. 3. Corresponding integers are denoted using the same reference numerals adopted in FIG. 1. H marks the approximate position of the hexaethylene residue incorporated in the split complement probe.

2.1 Preparation of Oligonucleotides

All oligonucleotide probes were prepared and functionalised as described in Example 1.1.

Hex incorporation was accomplished by reaction of the growing chain with 18-dimethoxytrityl hexaethylene glycol, 1-[(2-cyanoethyl)-(N,N-diisopropyl)]-phosphoramidite. All oligonucleotides were HPLC purified using standard techniques.

The oligonucleotides used were identical to those described in Example 1, with the exception of the variant Probe 3 (split complement) oligo (referred to below as "Probe 5"), which contained a Hex between the 11$^{th}$ and 12$^{th}$ bases (counting from the 5' end).

2.2 Synthesis of RNA Off Hybridised Oligonucleotides

Hybridisation was achieved in an assay mixture that contained 10 fmol of probe 1, 50 fmol of probe 2, 50 fmol of probe 3 or probe 5 (Hex containing variant of probe 3) and 1 fmol of probe 4 (target for CFTR gene), together with T7 RNA polymerase buffer (Promega). The reaction volume was made up to 20 µl with RNase-free distilled water (allowing for later additions of enzymes and NTPs). Control reactions contained probes 1, 2 and 3, or probes 1, 2 and 5, without target (probe 4). The mixture was heated to 90° C. for 3 minutes to denature the nucleic acids, then cooled (by ramping at 0.1° C./second) to 37° C. T7 RNA polymerase (25 units) and 2 µl rNTP mix (Amersham Pharmacia Biotech) were added and the mixture incubated at 37° C. for 3 hours.

2.3 Capture and Detection of Synthesised RNA

Figure 4:
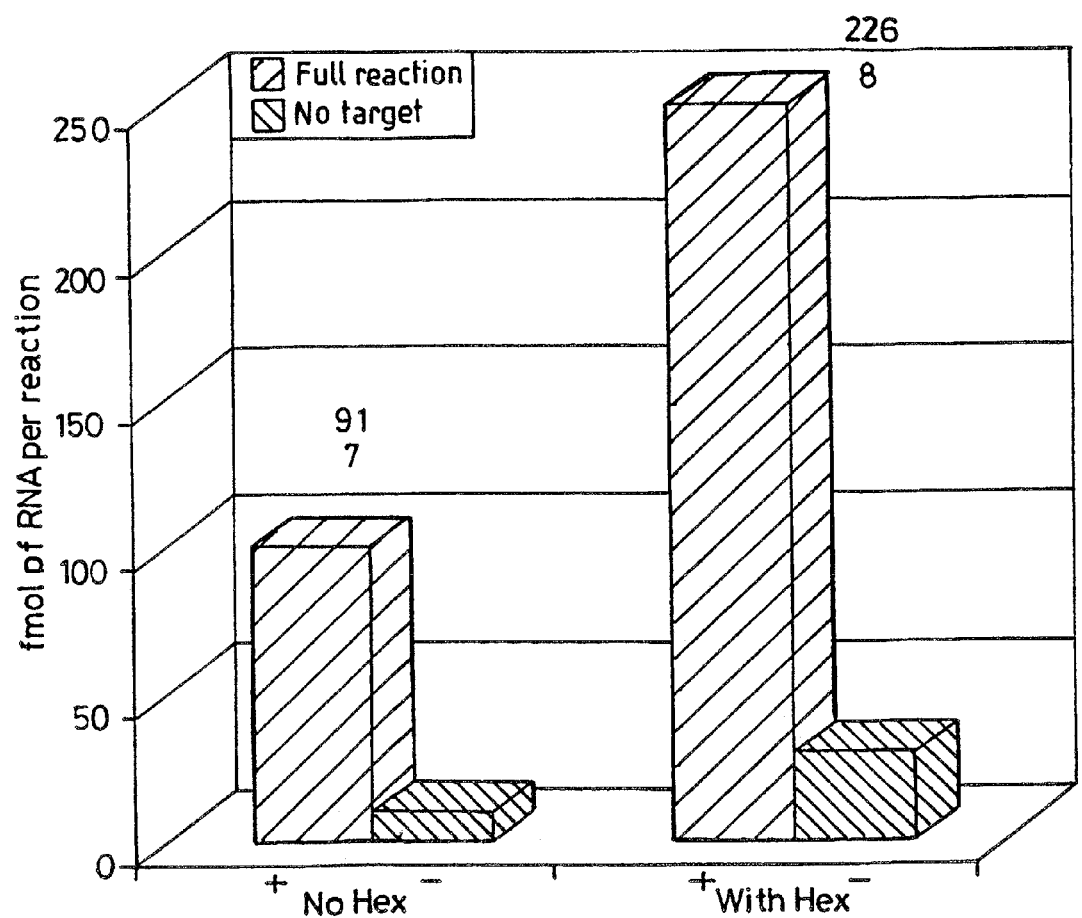
Figure 5:
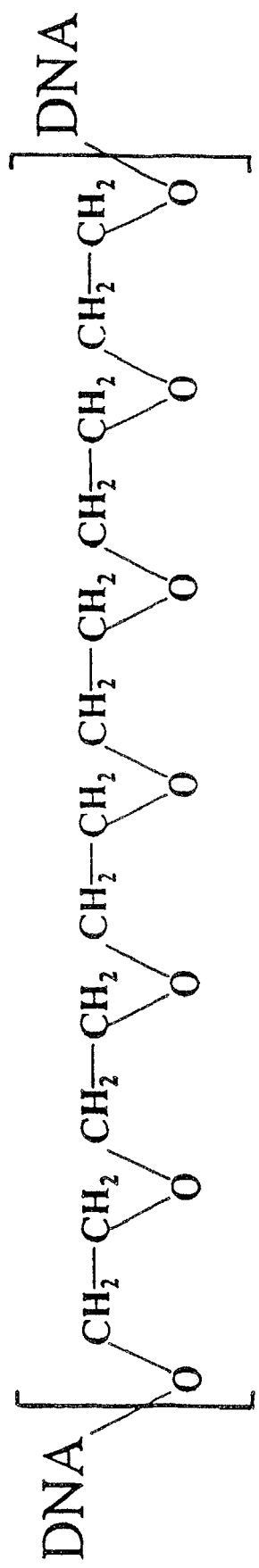
FIG. 5 is a schematic representation of a preferred destabilizing moiety for use in some embodiments of the invention.

20 µl of assay sample was processed as described in Example 1.3. Results are presented in FIG. 4, which is a chart showing amount of RNA produced in the presence (+) or absence (−) of target, for complexes without ("No Hex") or with a hexaethylene residue in the split complement probe.

EXAMPLE 3

This example demonstrated that increasing the length of the split complement probe at the 3' end by 1, 2 or 3 bases increased the amount of RNA signal observed.

3.1 Preparation of Oligonucleotides

All oligonucleotide probes were prepared and purified as described in the preceding examples.

3.2 Synthesis of RNA Off Hybridised Oligonucleotides

Hybridisation was achieved in an assay mixture that contained 10 fmol of probe 1, 50 fmol of probe 2, 50 fmol of probe 3 (14 base split complement), 4 (15 base split complement), 5 (16 base split complement) or 6 (17 base split complement) and 1 fmol of probe 7 (target for CFTR gene), together with T7 RNA polymerase buffer (Promega). All reactions also contained 50 ng salmon sperm DNA (Sigma) and 5% Polyethylene glycol 300 (Sigma). The reaction volume was made up to 20 µl with RNase-free distilled water (allowing for later additions of enzymes and NTPs). Control reactions contained probes 1, 2 and one of probes 4, 5 or 6, without target (probe 7). The mixture was heated to 90° C. for 3 minutes to denature the nucleic acids, then cooled (by ramping at 0.1° C./second) to 37° C. After 1 hr, T7 RNA polymerase (Promega) (25 units) and 2 µl rNTP mix (Amersham Pharmacia Biotech).

3.3 Capture and Detection of Synthesised RNA

Figure 6:
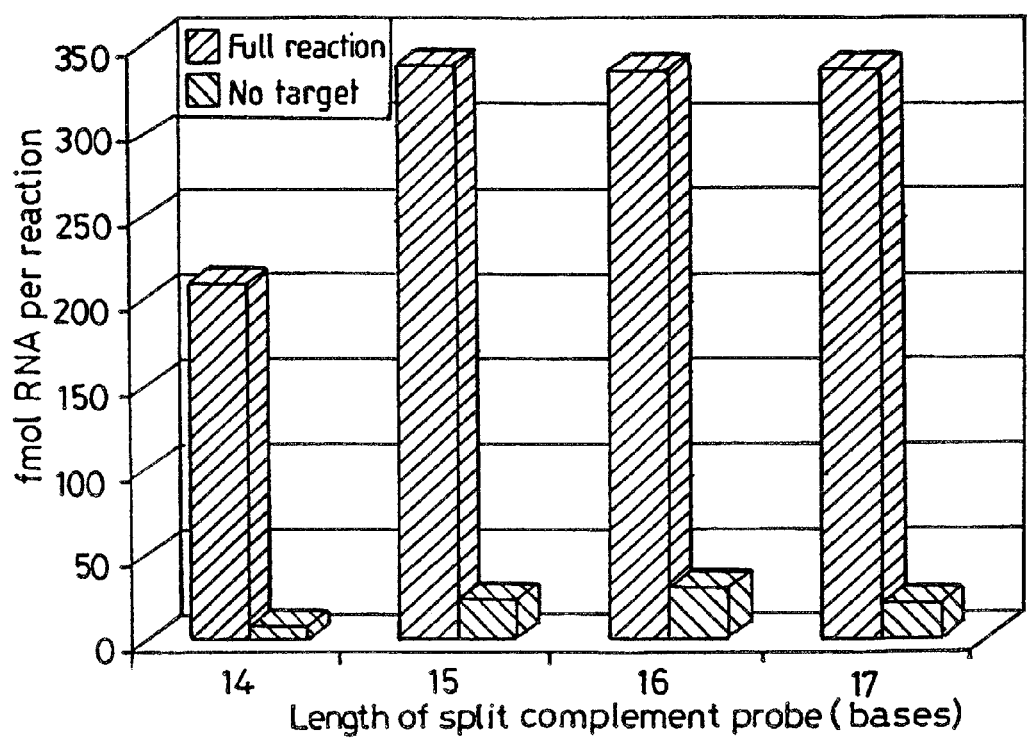

20 µl of assay sample was processed as described in Example 1.3. Results are presented in FIG. 6, which is a chart showing amount of RNA produced in reactions having a split complement probe of 14, 15, 16 or 17 bases in length.

3.4 List of Oligonucleotides
Probe 1 (template) (Seq ID No. 22)

5' TCGTCTTCCGGTCTCTCCTCTCAAGCCTCAGCGCTCTCTCTCCCTATAGTGAGT

CGTATTAATTTCGAAGGTGTTTCCTATGATGAATATAGATACAGAAGCG 3'

(phosphate blocked)

Probe 2 (complement)—as Probe 2, Example 1

Probe 3 (14 base split complement)—as Probe 3, Example 1

Probe 4 (15 base split complement)—as Probe 3, Example 1 but with additional G at 3' end Probe 5 (16 base split complement)—as Probe 3, Example 1 but with additional GG at 3'end Probe 6 (17 base split complement)—as Probe 3, Example 1 but with additional GGG at 3' end Probe 7 (target)—as Probe 4, Example 1

Sequence of transcribed RNA (Seq ID No. 23)

5' GGGAGAGAGAGCGCUGAGGCUUGAGAGGAGAGACCGGAAGACGA 3'

Capture Probe (Seq ID No. 24)

5' TCTGCTCGTCTTCCGGTCTCTCCTC 3'

(5' biotinylated)

Detection probe (Seq ID No. 25)

5' TCAAGCCTCAGC 3'

(3' alkaline phosphatase)

EXAMPLE 4

This example demonstrated that a three base deletion in a target sequence could be detected. The foot region of the complement probe was 30 bases whilst the foot region of the template probe was either 14 bases or 30 bases. The three base deletion was located 7 bases from the junction point on the template probe foot side of the junction.

4.1 Preparation of Oligonucleotides

All oligonucleotide probes were prepared and purified as described previously. Octanediol was incorporated by reaction of the growing chain with 8-dimethoxytrityl octanediol, 1-[(2-cyanoethyl)-(N,N-diisopropyl)]-phosphoramidite.

4.2 Synthesis of RNA Off Hybridised Oligonucleotides

Hybridisation was achieved in an assay mixture that contained 10 fmol of probe 1 (14 base template foot), 50 fmol of probe 3, 50 fmol of probe 4 and 1 fmol of probe 5 (wild type target sequence) or 1 fmol of probe 6 (mutant target sequence); 10 fmol of probe 2 (30 base template foot), 50 fmol of probe 3, 50 fmol of probe 4 and 1 fmol of probe 5 (wild type target sequence) or 1 fmol of probe 6 (mutant target sequence). All reactions also contained 50 ng salmon sperm DNA (Sigma) and 5% Polyethylene glycol 300 (Sigma). T7 RNA polymerase buffer (Promega) was added. The reaction volume was made up to 20 µl with RNase-free distilled water (allowing for later additions of enzymes and NTPs). Control reactions excluded the target (probe 5 or 6) The mixture was heated to 90° C. for 3 minutes to denature the nucleic acids, then cooled (by ramping at 0.1° C./second) to 37° C. After 1 hr, T7 RNA polymerase (Promega) (25 units) and 2 µl rNTP mix (Amersham Pharmacia Biotech) were added and the mixture incubated at 37° C. for 3 hours.

4.3 Capture and Detection of Synthesised RNA

Figure 7:
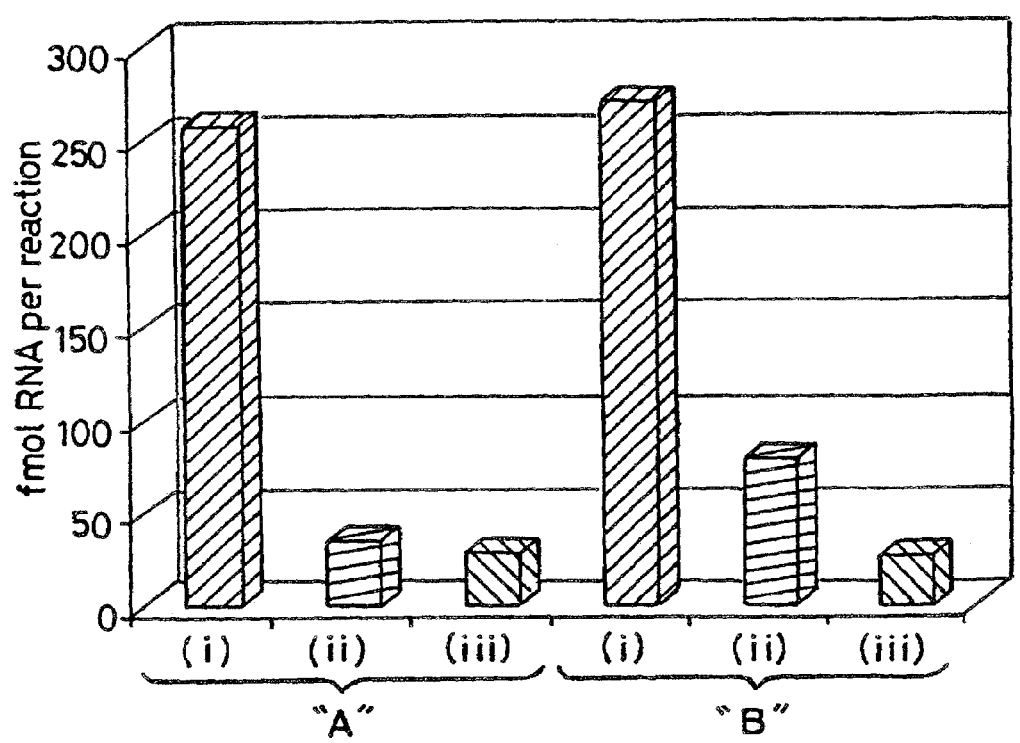

20 µl of assay sample was processed as described previously. Results are presented in FIG. 7. FIG. 7 shows the amount of RNA-produced for reactions in which the template comprised a 14 or 30 base foot region respectively ("A" and "B"), for wild type (i) or mutant (ii) target sequences, or controls (iii) with no target. The results demonstrate that it was readily possible to discriminate between the wild type and mutant targets.

4.4 List of Oligonucleotides
Probe 1 (template probe with a 14 base foot region) (Seq ID No. 26)

5' TCGTCTTCCGGTCTCTCCTCTCAAGCCTCAGCGCTCTCTCTCCCTATAGTG

AGTCGTATTAATTTCGAA<u>O</u>ATATCATCTTTGGT 3' (phosphate blocked)

O=Octanediol

Probe 2 (template probe with a 30 base foot region) (Seq ID No. 27)

5' TCGTCTTCCGGTCTCTCCTCTCAAGCCTCAGCGCTCTCTCTCCCTATAGTGAGT

CGTATTAATTTCGAA<u>O</u>ATATCATCTTTGGTGTTTCCTATGATGAAT 3'

O=Octanediol
Probe 3 (complement probe) (Seq ID No. 28)

5' GCCTGGCACCATTAAAGAAATTCGAAATTAA 3'

Probe 4 (split complement probe)—as Probe 4, Example 3
Probe 5 (wild type target sequence)—as Seq ID No. 18, Example 1

5' GTTGGCATGCTTTGATGACGCTTCTGTATCTATATTCATCATAGGAAACAC

CAAAGATGATATTTTCTTTAATGGTGCCAGGCATAATCCAGGAAAACTGAGAAC

AGAATGAAATTCTTC 3'

Bold text represents the 3 bases that are deleted in the mutant.
Probe 6 (mutant target sequence) (Seq ID No. 29)

5'GATGACGCTTCTGTATCTATATTCATCATAGGAAACACCAATGATATTTTCTT

TAATGGTGCCAGG CAT AAT CCA GG 3'

[Arrow represents the position of the 3 base deletion. The 3 base deletion is located 7 bases from the junction.]
Sequence of transcribed RNA (as Seq ID No. 23, Example 3)
Capture Probe (as Seq ID No. 24, Example 3)
Detection probe (as Seq ID No. 25, Example 3)

EXAMPLE 5

This example demonstrated that 23S rRNA in total RNA purified from *Escherichia coli* K12 could be detected.

5.1 Preparation of Oligonucleotides

All oligonucleotide probes were prepared and purified as described previously.

5.2 Preparation of Total RNA

*E. coli* was grown in Luria-Bertani medium (10 g $l^{-1}$ bacto-tryptone, 5 g $l^{-1}$ yeast extract and 10 g $l^{-1}$ sodium chloride) at 37° C. until the culture reached an $OD_6OC$ of 1.0. A Qiagen RNeasy® Mini Kit was used to purify the total RNA. Cells were harvested and lysed according to the manufacturer's instructions. RNA was quantified using GeneQuant II (Amersham Pharmacia Biotech) according to the manufacturer's instructions and aliquots were stored at −80° C. until ready for use.

5.3 Synthesis of RNA Off Hybridised Oligonucleotides

Hybridisation was achieved in an assay mixture that contained 1 fmol of probe 1, 5 fmol of probe 2, 5 fmol of probe 3 and 10, 1 or 0.1 ng of total RNA from *E. coli* K12. 50 ng salmon sperm DNA (Sigma) and 5% Polyethylene glycol 300 (Sigma) were also included in all reactions. T7 RNA polymerase buffer (Promega) was added and the reaction volume made up to 20 $\mu$l with RNase-free distilled water (allowing for later additions of enzymes and NTPs). Control reactions contained probes 1, 2 and 3 without any target RNA. The mixture was heated to 95° C. for 5 minutes and then cooled (by ramping at 0.1° C./second) to 37° C. After 1 hr. T7 RNA polymerase (Promega) (25 units) and 2 $\mu$l rNTP mix (Amersham Pharmacia Biotech) were added and the mixture incubated at 37° C. for 3 hours. The reactions were stored at −80° C.

5.4 Amplification of the RNA Signal

To further amplify the RNA transcribed from the T7 promoter in the complex, a linear DNA template (probe 4) was used, which contained a single stranded T7 promoter sequence. A 10 $\mu$l aliquot of each reaction was added to a mix containing 20 fmol of probe 4, 8 $\mu$l T7 RNA polymerase buffer, 50 $\mu$M dNTPs, 2 mM rNTPs, 51 Units T7 RNA polymerase and 4 Units Bst DNA polymerase. The volume was made up to 40 $\mu$l with RNase-free distilled water.

The mixture was incubated at 37° C. for 3 hours. The RNA from the initial reaction (5.3) hybridised with probe 4 and was extended by the Bst polymerase, forming a fully functional double stranded RNA promoter, which then produced multiple RNA transcripts of the second DNA template, probe 4.

5.5 Capture and Detection of Synthesised RNA

Figure 8:
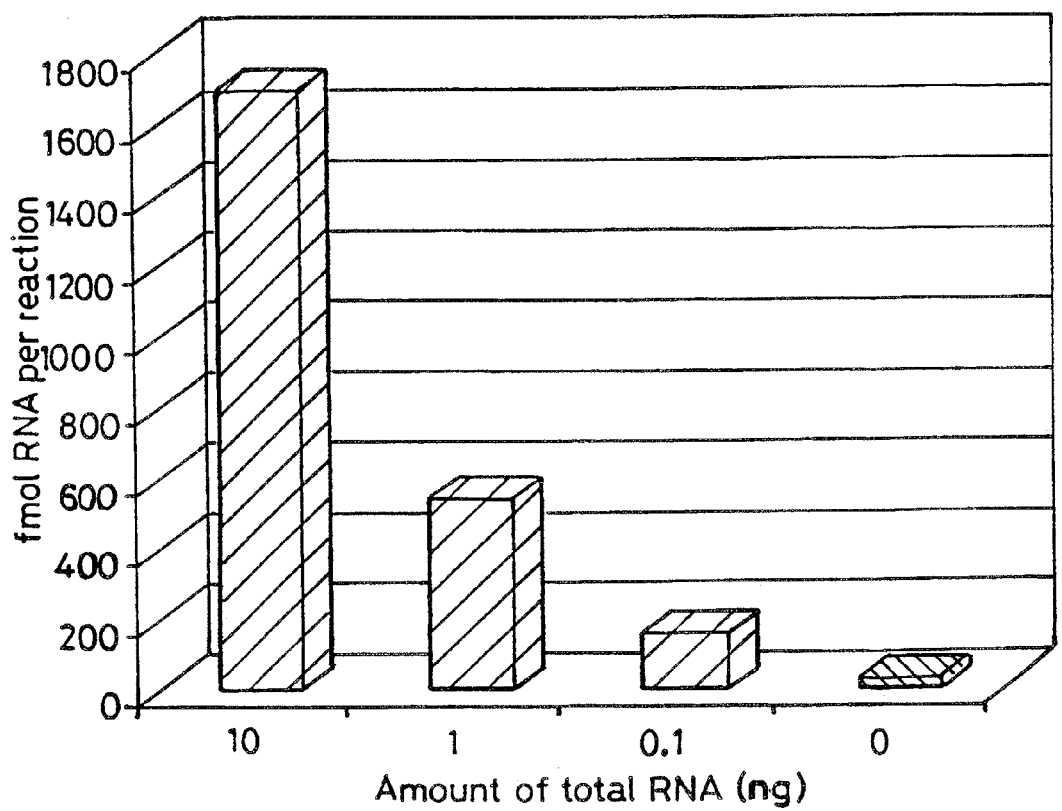

40 $\mu$l of assay sample was processed as described previously. Results are presented in FIG. 8. FIG. 8 shows the amount of RNA produced in reactions using varying amounts (10, 1 or 0.1 ng) of total RNA from *E. coli* K12 as target, compared with a control reaction (no target).

5.6 List of Oligonucleotides
Probe 1 (template probe) (Seq ID No. 30)

5' TCGTCTTCCGGTCTCTCCTCTCAAGCCTCAGCGCTCTCTCTCCCTATAGTG

AGTCGTATTAATTTCGAA<u>O</u>GGCATGACAACCCGAACACCAGTGAT 3'

O=Octanediol
Probe 2 (complement probe) (Seq ID No. 31)

5' GCATTTAGCTACCGGGCAGTGCCATTTTCGAAATTAA 3'

Probe 3 (split complement probe)—as Probe 4, Example 3
Probe 4 (2$^{nd}$ DNA template probe)—(Seq ID No. 32)

5' TGCCTGCTTGTCTGCGTTCTGGATATCACCCGAGTTCTCGCTTCCTATAGT

GAGTCGTATTAATTTCTCGTCTTCC<u>O</u>GGTCTCTCCTCTCAAGCCTCAGCGCTCTC

TCTCCC 3'

O=Octanediol
Sequence of transcribed RNA to be Detected (Seq ID No. 33)

5' GGAAGCGAGAACUCGGGUGAUAUCCAGAACGCAGACAAGCAGGCA 3'

Capture Probe—as Seq ID No. 20, Example 1
Detection probe—as Seq ID No. 21, Example 1

EXAMPLE 6

This example demonstrated that a T3 promoter and T3 RNA polymerase could be used instead of a T7 promoter and T7 RNA polymerase. A 14 base split complement probe was used for the 17 base T3 promoter.

6.1 Preparation of Oligonucleotides

All oligonucleotide probes were prepared and purified as described previously.

6.2 Synthesis of RNA Off Hybridised Oligonucleotides

For the assay containing a T7 promoter, 10 fmol probe 1, 50 fmol probe 2, 50 fmol probe 3 and 1 fmol probe 4 were used. For the assay containing a T3 promoter, 10 fmol probe 5, 50 fmol probe 6, 50 fmol probe 7 and 1 fmol probe 4 were used. 50 ng salmon sperm DNA (Sigma) and 5% Polyethylene glycol 300 (Sigma) were also included in all reactions. T7 RNA polymerase buffer (Promega) was used with both T7 (Promega) and T3 RNA polymerases (Promega) and the reaction volume made up to 20 μl with RNase-free distilled water (allowing for later additions of enzymes and NTPs). Control reactions contained probes 1, 2 and 3 or probes 5, 6 and 7. The mixture was heated to 90° C. for 3 minutes and then cooled (by ramping at 0.1° C./second) to 37° C. After 1 hr, T7 RNA polymerase (25 units) or T3 RNA polymerase (25 units) and 2 μl rNTP mix (Amersham Pharmacia Biotech) were added and the mixture incubated at 37° C. for 3 hours. The reactions were stored at −80° C.

6.3 Capture and Detection of Synthesised RNA

20 μl of assay sample was processed as described previously. Results are presented in FIG. 9.

Figure 9:
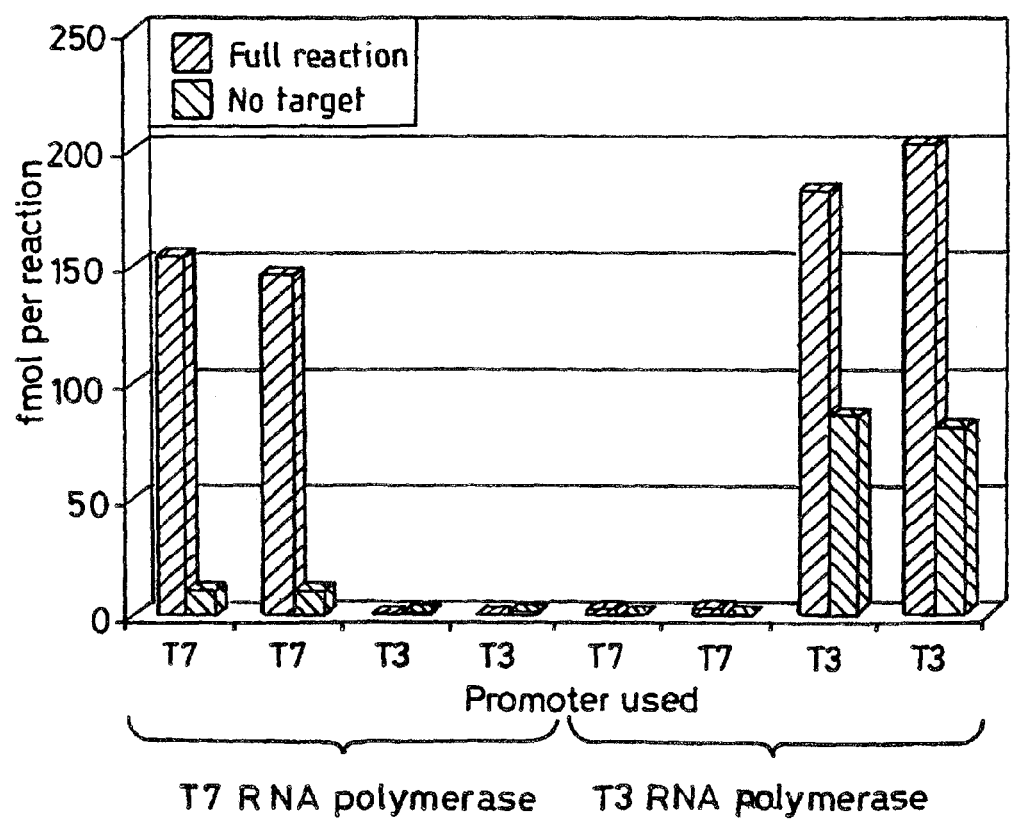

FIG. 9 shows the amount of RNA produced in reactions using T7 or T3 RNA polymerase. As expected, the reaction was specific in that T7 RNA polymerase would only produce RNA from a T7 promoter, not from a T3 promoter; and vice versa for T3 RNA polymerase. T3 polymerase produced slightly more RNA than T7 polymerase but, in this system, the background signal (in the absence of target) was much higher for T3.

List of Oligonucleotides
Probe 1 (T7 template) (Seq ID No. 34)

5' TCGTCTTCCGGTCTCTCCTCTCAAGCCTCAGCCTTCTCTCTTCCTATAGTG

AGTCGTATTAATTTCGAAGGTGTTTCCTATGATGAATATAGATACAGAAGCG 3'

Probe 2 (T7 complement)—as Seq ID No. 16, Example 1
Probe 3 (T7 split complement)—as Seq ID No. 17, Example 1
Probe 4 (target) (Seq ID No. 35)

5' CCTCCTCTAGTTGGCATGCTTTGATGACGCTTCTGTATCTATATTCATCAT

AGGAAACACCAAAGATGATATTTTCTTTAATGGTGCCAGGCATAATCCAGGAAA

ACTGAGAACAGAATGA 3'

Probe 5 (T3 template) (Seq ID No. 36)

5' TCGTCTTCCGGTCTCTCCTCTCAAGCCTCAGCCTTCTCTCTTCCTTTAG

TGAGGGTTAATTATTTCGAAGGTGTTTCCTATGATGAATATAGATACAGAAGCG

3'

Probe 6 (T3 complement) (Seq ID No. 37)

5' GCCTGGCACCATTAAAGAAAATATCATCTTTTTCGAAATAAT 3'

Probe 7 (T3 split complement) (Seq ID No. 38)

5' TAACCCTCACTAAA 3'

Sequence of transcribed RNA (Seq ID No. 39)

```
5' GGAA GAG AGA AGG CUG AGG CUU GAGAGGAGAGACCGGAAGACGA 3'
```

Capture Probe—as Seq ID No. 24, Example 3
Detection probe—as Seq ID No. 25, Example 3

EXAMPLE 7

Figure 10:
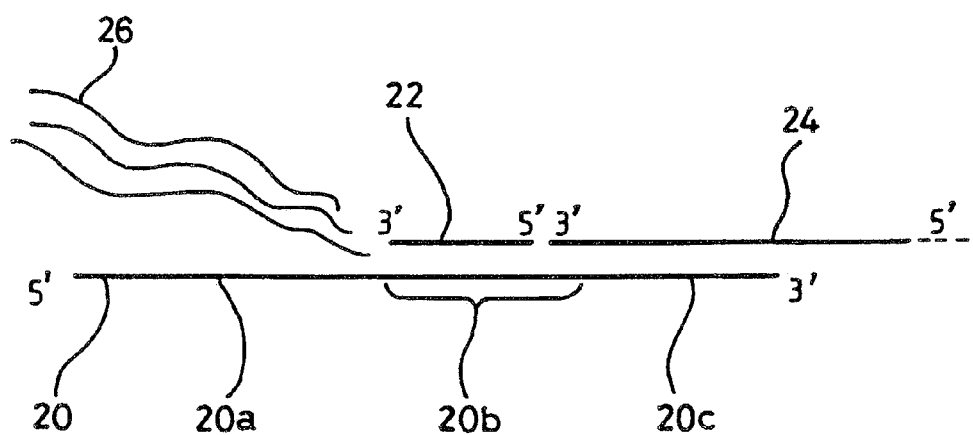
FIG. 10 is a schematic representation of a nucleic acid complex in accordance with the third aspect of the invention.

This example illustrates the complex of the third aspect of the invention, by reference to FIG. 10.

Referring to FIG. 10, a complex comprises a first probe 20, a second probe 22 and a target nucleic acid 24. The first probe 20 comprises a transcribable portion 20a, a template strand 20b of an RNA polymerase promoter (such as the T3, T7 or SP6 RNA promoter), and a target complementary portion 20c which is hybridised to 3' end of the target sequence 24.

The second probe 22 is hybridised to the first probe 20 adjacent to the target sequence 24. The second probe 22 comprises bases which are complementary to part (preferably the majority, e.g. 13–15 bases) of the template strand of the promoter on first probe 20 (i.e. the second probe 22 comprises *part*, preferably the *majority*, of the *non-template* strand of the *promoter*). T*he* remainder of the *non-template* strand (*typically* 4–2 bases) is contributed by the 3' end of the target sequence 24. Accordingly, the complex is such that it comprises a functional double stranded RNA polymerase promoter which, in the presence of a relevant RNA polymerase and ribonucleotide triphosphates, causes synthesis of RNA transcripts 26 of the template portion 20a of the first probe.

The RNA transcripts 26 may be detected, preferably following an optional amplification step, to indicate the presence of the target sequence 24, which may be the sequence of interest or which may have been generated in turn by the presence of the sequence of interest (e.g. by PCR, or by means of one of the other processes described in the prior art, such as WO 93/06240, WO 94/29481 or EP 0851033).

What is claimed is:

1. A complex formed by a hybridisation reaction comprising four nucleic acid molecules; the complex comprising a target nucleic acid molecule and first, second and third nucleic acid probe molecules; wherein the first probe comprises a foot region which is complementary to a first portion of the target and is hybridised thereto, and an arm region which is substantially non-complementary to the target; the second probe comprises a foot region which is complementary to a second portion of the target, such that the foot region of the second probe is hybridised to the target adjacent or substantially adjacent to the foot region of the first probe, the second probe also comprising an arm region which is substantially non-complementary to the target but which is complementary and hybridised to the arm region of the first probe; the third probe being complementary, at least in part, to a portion of the arm region of the first probe such that the third probe is hybridised to the arm region of the first probe adjacent or substantially adjacent to the second probe; and wherein formation of the complex creates a functional double-stranded RNA polymerase promoter, one strand of the promoter being provided by the first probe, and the other strand being provided jointly by the second probe and by the third probe.

2. A complex according to claim 1, wherein at least one of the first, second or third probes comprises PNA and/or LNA.

3. A complex according to claim 2, wherein the first and/or second probe comprises PNA and/or LNA.

4. A complex according to claim 1, comprising a functional double stranded T3, T7 or SP6 RNA polymerase promoter.

5. A complex according to claim 1, comprising single or double stranded sequence adjacent to the promoter which increases the activity of the promoter.

6. A complex according to claim 5, wherein one of said probes comprises a +12 sequence.

7. A complex according to claim 5, wherein the first probe comprises a +12 sequence.

8. A complex according to claim 1, comprising a sequence which, when transcribed into RNA, facilitates isolation, identification, detection, quantification or amplification of the transcript.

9. A complex according to claim 1, wherein one of said probes comprises a destabilizing moiety.

10. A complex according to claim 1, wherein the second and third probes form a discontinuous sequence of an RNA polymerase promoter template strand.

11. A complex according to claim 1, wherein the second and third probes form a discontinuous sequence of an RNA polymerase promoter non-template strand.

12. A method of detecting the presence of a target nucleic acid molecule in a sample, the method comprising the steps of: contacting the sample comprising the target with first and second nucleic acid probes, each probe comprising a foot region complementary to respective first and second portions of the target, which portions are adjacent or substantially so; wherein the first and second probes each further comprise an arm region substantially non-complementary to the target, at least part of the arm region of the first probe being complementary to at least part of the arm region of the second probe, such that respective foot regions of the first and second probes hybridise to the target, allowing hybridisation of the complementary parts of the arm regions of the first and second probes; and causing to be present a third nucleic acid probe molecule which is complementary to a portion of the arm region of the first probe, such that the third probe hybridises to the first probe adjacent or substantially adjacent to the arm region of the second probe, thereby creating a functional double-stranded RNA polymerase promoter, one strand of the promoter being provided by the first probe, the other strand being provided jointly by the second and third probes; causing RNA synthesis from the RNA promoter; and detecting, directly or indirectly, the RNA so synthesised, wherein the synthesized RNA indicates the presence of the target nucleic acid molecule in the sample.

13. The method according to claim 12, performance of which results in the formation of a complex formed by a hybridization reaction comprising four nucleic acid molecules.

14. The method according to claim 12, wherein RNA produced from the functional RNA promoter is amplified prior to detection.

15. The method according to claim 12, wherein RNA produced from the functional RNA promoter is detected directly or indirectly via a method which involves use of a molecular beacon or fluorophore.

16. A kit comprising a first probe and a third probe molecule according to claim 1.

17. A kit comprising a second probe and a third probe molecule according to claim 1.

18. A kit comprising a first, second and third probe molecule according to claim 1.

* * * * *

SEQUENCE LISTING

```
<160> NUMBER OF SEQ ID NOS: 39

<210> SEQ ID NO 1
<211> LENGTH: 18
<212> TYPE: DNA
<213> ORGANISM: Bacteriophage T3

<400> SEQUENCE: 1
aaattaaccc tcactaaa                                              18

<210> SEQ ID NO 2
<211> LENGTH: 18
<212> TYPE: DNA
<213> ORGANISM: Bacteriophage T3

<400> SEQUENCE: 2
ttattaaccc tcactaaa                                              18

<210> SEQ ID NO 3
<211> LENGTH: 17
<212> TYPE: DNA
<213> ORGANISM: Bacteriophage T7

<400> SEQUENCE: 3
taatacgact cactata                                               17

<210> SEQ ID NO 4
<211> LENGTH: 17
<212> TYPE: DNA
<213> ORGANISM: Bacteriophage SP6

<400> SEQUENCE: 4
atttaggtga cactata                                               17

<210> SEQ ID NO 5
<211> LENGTH: 12
```

```
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 5
atcgtcagtc cc                                                           12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
gctctctctc cc                                                           12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
atcctctctc cc                                                           12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
gttctctctc cc                                                           12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
gatgtgtctc cc                                                           12

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
gttgtgtctc cc                                                           12

<210> SEQ ID NO 11
<211> LENGTH: 12
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 11
atcctcgtgc cc                                                           12

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12
gctctcgtgc cc                                                           12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
gttctcgtgc cc                                                           12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
gttgtggtgc cc                                                           12

<210> SEQ ID NO 15
<211> LENGTH: 108
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
tgcctccttg tctccgttct ggatatcacc cgatgtggct ctctctccct atagtgagtc       60
gtattaattt cgaaggtgtt tcctatgatg aatatagata cagaagcg                   108

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
gcctggcacc attaaagaaa atatcatctt tttcgaaatt aa                          42

<210> SEQ ID NO 17
<211> LENGTH: 14
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 17
tacgactcac tata                                                           14

<210> SEQ ID NO 18
<211> LENGTH: 120
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 18
gttggcatgc tttgatgacg cttctgtatc tatattcatc ataggaaaca ccaaagatga         60
tattttcttt aatggtgcca ggcataatcc aggaaaactg agaacagaat gaaattcttc        120

<210> SEQ ID NO 19
<211> LENGTH: 49
<212> TYPE: RNA
<213> ORGANISM: Artificial Sequence
<220> FEATURE:
<223> OTHER INFORMATION: Description of Artificial Sequence: RNA
      transcript of synthetic oligonucleotide

<400> SEQUENCE: 19
gggagagaga gccacaucgg gugauaucca gaacggagac aaggaggca                     49

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
tctgctgcct gcttgtctgc gttct                                               25

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
ggatatcacc cg                                                             12

<210> SEQ ID NO 22
<211> LENGTH: 103
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
tcgtcttccg gtctctcctc tcaagcctca gcgctctctc tccctatagt gagtcgtatt         60
aatttcgaag gtgtttccta tgatgaatat agatacagaa gcg                          103
```

```
<210> SEQ ID NO 23
<211> LENGTH: 44
<212> TYPE: RNA
<213> ORGANISM: Artificial Sequence
<220> FEATURE:
<223> OTHER INFORMATION: Description of Artificial Sequence: RNA
      transcript of synthetic oligonucleotide

<400> SEQUENCE: 23
gggagagaga gcgcugaggc uugagaggag agaccggaag acga                        44

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24
tctgctcgtc ttccggtctc tcctc                                             25

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
tcaagcctca gc                                                           12

<210> SEQ ID NO 26
<211> LENGTH: 83
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 26
tcgtcttccg gtctctcctc tcaagcctca gcgctctctc tccctatagt gagtcgtatt       60
aatttcgaaa tatcatcttt ggt                                               83

<210> SEQ ID NO 27
<211> LENGTH: 99
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 27
tcgtcttccg gtctctcctc tcaagcctca gcgctctctc tccctatagt gagtcgtatt       60
aatttcgaaa tatcatcttt ggtgtttcct atgatgaat                              99

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28
```

```
gcctggcacc attaaagaaa ttcgaaatta a                            31

<210> SEQ ID NO 29
<211> LENGTH: 77
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 29
gatgacgctt ctgtatctat attcatcata ggaaacacca atgatatttt ctttaatggt    60
gccaggcata atccagg                                                   77

<210> SEQ ID NO 30
<211> LENGTH: 95
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 30
tcgtcttccg gtctctcctc tcaagcctca gcgctctctc tccctatagt gagtcgtatt    60
aatttcgaag gcatgacaac ccgaacacca gtgat                               95

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 31
gcatttagct accgggcagt gccattttcg aaattaa                             37

<210> SEQ ID NO 32
<211> LENGTH: 111
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 32
tgcctgcttg tctgcgttct ggatatcacc cgagttctcg cttcctatag tgagtcgtat    60
taatttctcg tcttccggtc tctcctctca gcctcagcg ctctctctcc c              111

<210> SEQ ID NO 33
<211> LENGTH: 45
<212> TYPE: RNA
<213> ORGANISM: Artificial Sequence
<220> FEATURE:
<223> OTHER INFORMATION: Description of Artificial Sequence: RNA
      transcript of synthetic oligonucleotide

<400> SEQUENCE: 33
ggaagcgaga acucggguga uauccagaac gcagacaagc aggca                    45

<210> SEQ ID NO 34
<211> LENGTH: 103
<212> TYPE: DNA
<213> ORGANISM: Artificial Sequence
```

-continued

```
<220> FEATURE:
<223> OTHER INFORMATION: Description of Artificial Sequence: synthetic
      oligonucleotide

<400> SEQUENCE: 34
tcgtcttccg gtctctcctc tcaagcctca gccttctctc ttcctatagt gagtcgtatt      60
aatttcgaag gtgtttccta tgatgaatat agatacagaa gcg                       103

<210> SEQ ID NO 35
<211> LENGTH: 121
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 35
cctcctctag ttggcatgct ttgatgacgc ttctgtatct atattcatca taggaaacac      60
caaagatgat attttcttta atggtgccag gcataatcca ggaaaactga gaacagaatg     120
a                                                                     121

<210> SEQ ID NO 36
<211> LENGTH: 103
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 36
tcgtcttccg gtctctcctc tcaagcctca gccttctctc ttcctttagt gagggttaat      60
tatttcgaag gtgtttccta tgatgaatat agatacagaa gcg                       103

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 37
gcctggcacc attaaagaaa atatcatctt tttcgaaata at                         42

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 38
taaccctcac taaa                                                        14

<210> SEQ ID NO 39
<211> LENGTH: 44
<212> TYPE: RNA
<213> ORGANISM: Artificial Sequence
<220> FEATURE:
<223> OTHER INFORMATION: Description of Artificial Sequence: RNA
      transcript of  synthetic oligonucleotide

<400> SEQUENCE: 39
ggaagagaga aggcugaggc uugagaggag agaccggaag acga                       44
```